US012797552B2

(12) United States Patent
Calderwood et al.

(10) Patent No.: US 12,797,552 B2
(45) Date of Patent: Nov. 17, 2026

(54) VISUALLY COMMUNICATING MEDICAMENT DELIVERY INSTRUCTIONS

(71) Applicant: SHL Medical AG, Zug (CH)

(72) Inventors: Gary Calderwood, Nacka Strand (SE); Torbjörn Neby, Nacka Strand (SE)

(73) Assignee: SHL Medical AG, Zug (CH)

( * ) Notice: Subject to any disclaimer, the term of this patent is extended or adjusted under 35 U.S.C. 154(b) by 330 days.

(21) Appl. No.: 18/718,535

(22) PCT Filed: Dec. 16, 2022

(86) PCT No.: PCT/EP2022/086441

§ 371 (c)(1),
(2) Date: Jun. 11, 2024

(87) PCT Pub. No.: WO2023/117788

PCT Pub. Date: Jun. 29, 2023

(65) Prior Publication Data

US 2025/0041524 A1 Feb. 6, 2025

(30) Foreign Application Priority Data

Dec. 22, 2021 (EP) .................................... 21217157

(51) Int. Cl.
*A61M 5/31* (2006.01)

(52) U.S. Cl.
CPC ... *A61M 5/3146* (2013.01); *A61M 2005/3125* (2013.01)

(58) Field of Classification Search
CPC ........... A61M 2005/31508; A61M 2005/3125; A61M 5/178; A61M 5/24; A61M 5/2422
See application file for complete search history.

(56) References Cited

U.S. PATENT DOCUMENTS

| | | | |
|---|---|---|---|
| 4,968,299 A | 11/1990 | Ahlstrand | |
| 6,106,501 A | 8/2000 | Michel | |

(Continued)

FOREIGN PATENT DOCUMENTS

| | | | | |
|---|---|---|---|---|
| EP | 1185322 B1 | 12/2005 | | |
| EP | 3275479 A1 * | 1/2018 | ............... | G09F 3/02 |

(Continued)

OTHER PUBLICATIONS

International Search Report and Written Opinion for corresponding PCT application No. PCT/EP2022/086441 dated Apr. 4, 2023.

*Primary Examiner* — Laura A Bouchelle
(74) *Attorney, Agent, or Firm* — McDonnell Boehnen Hulbert & Berghoff LLP

(57) ABSTRACT

The present disclosure relates to a sub-assembly of a medicament delivery device comprising a main body configured to accommodate a medicament, a plunger rod being moveable inside the main body along a length of the main body upon a user applying force to the plunger rod, and wherein the main body comprises a window through which the plunger rod is observable upon moving along said length, the main body further being provided with medicament delivery instructions along the length of an exterior of the main body, wherein the medicament delivery instructions are configured to instruct the user to move the plunger rod further into the main body to align a first visual indication of the plunger rod observable through said window with a next medicament delivery instruction to be performed along the length of the main body.

15 Claims, 10 Drawing Sheets

(56) References Cited

U.S. PATENT DOCUMENTS

| | | | |
|---|---|---|---|
| 6,193,698 B1 | 2/2001 | Kirchhofer | |
| 6,331,173 B1 | 12/2001 | Ljungquist | |
| 8,439,864 B2 | 5/2013 | Galbraith | |
| 10,525,204 B2 * | 1/2020 | Blancke ............ | A61M 5/31551 |
| 2005/0261634 A1 | 11/2005 | Karlsson | |
| 2016/0325047 A1 | 11/2016 | Vedrine | |
| 2019/0380917 A1 | 12/2019 | Meola | |

FOREIGN PATENT DOCUMENTS

| | | |
|---|---|---|
| WO | 2005072796 A2 | 8/2005 |
| WO | 2019197493 A1 | 10/2019 |
| WO | 2021094797 A1 | 5/2021 |

* cited by examiner

VISUALLY COMMUNICATING MEDICAMENT DELIVERY INSTRUCTIONS

TECHNICAL FIELD

The present disclosure relates to a sub-assembly of a medicament delivery device.

CROSS-REFERENCE TO RELATED APPLICATIONS

The present application is a U.S. National Phase application pursuant to 35 U.S.C. § 371 of International Application No. PCT/EP2022/086441 filed Dec. 16, 2022, which claims priority to European Patent Application No. 21217157.3 filed Dec. 22, 2021. The entire disclosure contents of these applications are herewith incorporated by reference into the present application.

BACKGROUND

Using a medicament delivery device such as an injector to deliver a medicament is generally not an intuitive and straightforward process.

As a consequence, a medicament delivery instruction manual will typically have to be provided with the injector for a user to correctly operate the injector for medicament delivery.

It may even be envisaged that the user must be trained for operating the injector to perform medicament delivery, which is a time and resource-consuming process. US2016/325047 and WO2005/072796 both disclose an instruction arrangement of a medicament delivery device to guide the user for operating the injection. However, the instruction signs as disclosed are placed in a narrow space between a thumb pad/hand-operating part and the device body. It might be difficult to be seen by the users.

SUMMARY

One objective is to solve, or at least mitigate, this problem in the art and thus to provide an improved medicament delivery device which can be intuitively operated by the user to deliver a medicament.

This objective is attained in an aspect by a sub-assembly of a medicament delivery device comprising: a main body configured to accommodate a medicament; a plunger rod being moveable inside the main body along a length of the main body upon a user applying force to the plunger rod. The main body comprises a main window through which the accommodated medicament is observable; the main body further being provided with multiple medicament delivery instructions along the length of an exterior of the main body. Each of the medicament delivery instructions is configured to instruct the user to move the plunger rod further into the main body with a type of movement to align a first visual indication of the plunger rod observable through said main window with a next medicament delivery instruction to be performed along the length of the main body. The plunger rod comprises an engagement member at the exterior of the plunger rod; and the main body is operably arranged with a counter-engagement member at the interior of the main body. The plunger rod is configured to move into the main body via engagement between the engagement member and the counter-engagement member. The engagement member is one of a track and at least one rib, and the counter-engagement member is the other one of the track and the at least one rib. The track comprises multiple sections. Each of the multiple sections is shaped to guide the plunger rod to be moved with a type of movement relative to the main body such that the plunger rod can only be moved in the proximal direction with the type of movement. Each section of the track is arranged at a location relative to a location of one of the medicament delivery instructions such that the user can only perform the type of movement instructed by the instruction aligned with the first visual indication of the plunger rod to move the plunger rod in the proximal direction.

Advantageously, the user is given clear and straightforward instructions on how to administer the medicament on the main body of the medicament delivery device itself by both visual indication and action limitations, thus without burden performing administration of the medicament as indicated by the instructions. Furthermore, as the main window is usually the biggest window of a medicament delivery device as most of the drug regulations request the accommodated medicament to be clearly observable by the user, using the main window to provide visual indication of the operation steps allows the user to easily observe the indication. Furthermore, when the medicament delivery device needs to be prepared by mixing substances from two different chambers of a medicament container of the medicament delivery device, the user can observe the status of mixing, e.g., whether the solid substance is fully dissolved before performing the next step of the device operation.

In an embodiment, the main body comprises a second window through which the plunger rod is observable upon moving along the length of the main body, the main window and the second window being arranged on a same side of the main body and aligned with respect to a longitudinal axis of the main body.

In an embodiment, the plunger rod is arranged with at least one second visual indication on an exterior of the plunger rod, and a second window of the at least two windows is configured to display the at least one second visual indication while a main window of the at last two windows is configured to display the first visual indication of the plunger rod, said at least one second visual indication being related to the medicament delivery instruction with which the first visual indication of the plunger rod currently is aligned. Advantageously, this enables presenting complementing information to the user.

In an embodiment, the at least one second visual indication comprises one or more of an hourglass symbol, a confirmation symbol, a lock symbol, and an unlock symbol.

In an embodiment, the main body comprises a counter-engagement member at the interior of the main body.

In an embodiment, an insert is attached to the main body, wherein the insert comprises the counter-engagement member to engage with said engagement member.

In an embodiment, each of the multiple sections are shaped to guide the plunger rod to be moved with a linear movement or a helical movement relative to the main body such that the plunger rod is moved in the proximal direction with the linear movement or the helical movement.

In an embodiment, the track comprises at least one first axial groove connecting to one end of a helical groove and at least one second axial groove connecting to another end of the helical groove.

In an embodiment, the track further comprises a circumferential groove connecting to the at least one second axial groove at one end of the circumferential groove, and at least one third axial groove connecting to the circumferential groove at another end of the circumferential groove, the circumferential groove further extending in an axial direction.

In an embodiment, the plunger rod is configured to move further into the main body with a rotation relative to the main body via engagement between the at least one rib and the helical groove and with an axial push into the main body via engagement between the at least one rib and either one of the at least one first axial groove, the at least one second axial groove, the circumferential groove and the at least one third axial groove.

In an embodiment, an inner wall of the helical groove comprises at least one first stop surface at the end connecting to said at least one first axial groove for blocking the at least one rib from further axial movement as a next movement, and a second stop surface at the end connecting to said at least one second axial groove for blocking the at least one rib from further rotational movement as a next movement, the circumferential groove comprises at least one first radially protruding stop surface at the end connecting to said at least one third axial groove for blocking the at least one rib from further axial movement as a next movement, and at least one second radially protruding stop surface along a circumferential axis for blocking the at least one rib from further rotational axial movement as a next movement after a 180° rotational movement have been performed upon said at least one rib member being blocked by the at least one first radially protruding stop surface of the circumferential groove, and the at least one third axial groove comprises at least one first radially protruding stop surface for blocking the at least one rib from any further movement into the main body. Advantageously, if one movement is enabled by rotation of the plunger rod, a next movement is enabled by an axial push (and vice versa), making the administration process simple and intuitive to follow for the user.

In an embodiment, the at least one first axial groove, the helical groove, the at least one second axial groove, the circumferential groove and the at least one third axial groove comprises at least one bump over which the at least one rib traverses upon the user moving the plunger rod into the main body.

In an embodiment, the track comprises at least one bump over which the at least one rib traverses upon the user moving the plunger rod into the main body.

In an embodiment, the track comprises multiple bumps being arranged along the track at locations relative to locations of the medicament delivery instructions such that the bumps are traversed by the at least one rib one after another before the first visual indication aligns with a medicament delivery instruction along the main body and after the first visual indication moves out of alignment with the medicament delivery instruction along the main body.

Advantageously, the bump(s) provide tactile and/or audible feedback to the user upon the rib(s) traversing the bumps. The bumps are typically located along the plunger rod such that the ribs traverse the bumps one after another just before the first visual indication moves into alignment with an instruction and just after the first visual indication moves out of alignment with the instruction.

In an embodiment, each bump is arranged with a first side having a surface with an increasing inclination in a direction via which the at least one rib traverses the bump, and an opposite second side having a surface facing a direction of movement of the at least one rib and forming an abutment with a counter surface of the at least one rib upon reverse movement of the plunger rod. Advantageously, the bumps are configured such that the rib can traverse the bump upon the user moving the plunger rod into the main body, but prevent the user from reversely moving the plunger rod out of the main body.

In an embodiment, a label is attached to the exterior of the main body, the label comprising said medicament delivery instructions.

In an embodiment, the medicament delivery instructions are integrated on the exterior of the main body.

In an embodiment, the first visual indication is formed by a proximal end of the plunger rod being pushed further into the main body.

In an embodiment, the multiple medicament delivery instructions are one of printed instructions on the main body, printed instructions attached to the main body, instructions formed by multiple protrusions extending from the main body, instructions formed by multiple recesses in a wall of the main body, and instructions formed by multiple protrusions attached to the main body.

In an embodiment, the first visual indication is arranged at the proximal end of the plunger rod.

In an embodiment, the medicament delivery device is an injection device.

In an embodiment, the injection device comprises a medicament container.

In an embodiment, the container comprises two chambers containing two different medicaments.

In an embodiment, the container is a glass cartridge or a collapsible bag.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

Aspects and embodiments are now described, by way of example, with reference to the accompanying drawings, in which.

DETAILED DESCRIPTION

The aspects of the present disclosure will now be described more fully hereinafter with reference to the accompanying drawings, in which certain embodiments of the invention are shown.

These aspects may, however, be embodied in many different forms and should not be construed as limiting; rather, these embodiments are provided by way of example so that this disclosure will be thorough and complete, and to fully convey the scope of all aspects of the invention to those skilled in the art. Like numbers refer to like elements throughout the description.

Figure 1A:
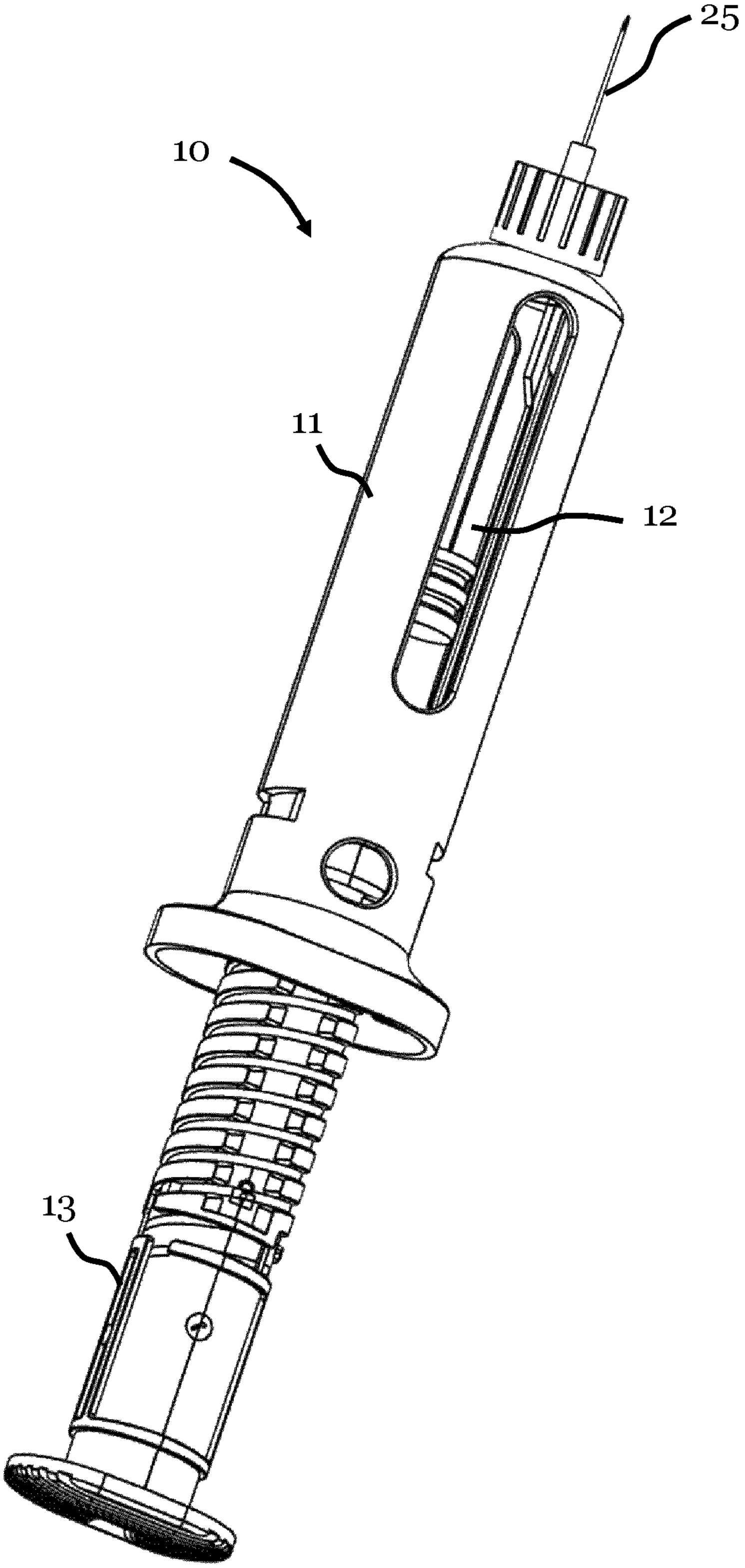
FIG. 1A shows a perspective view illustrating a medicament delivery device in the form of an injector according to an embodiment.
Figure 1B:
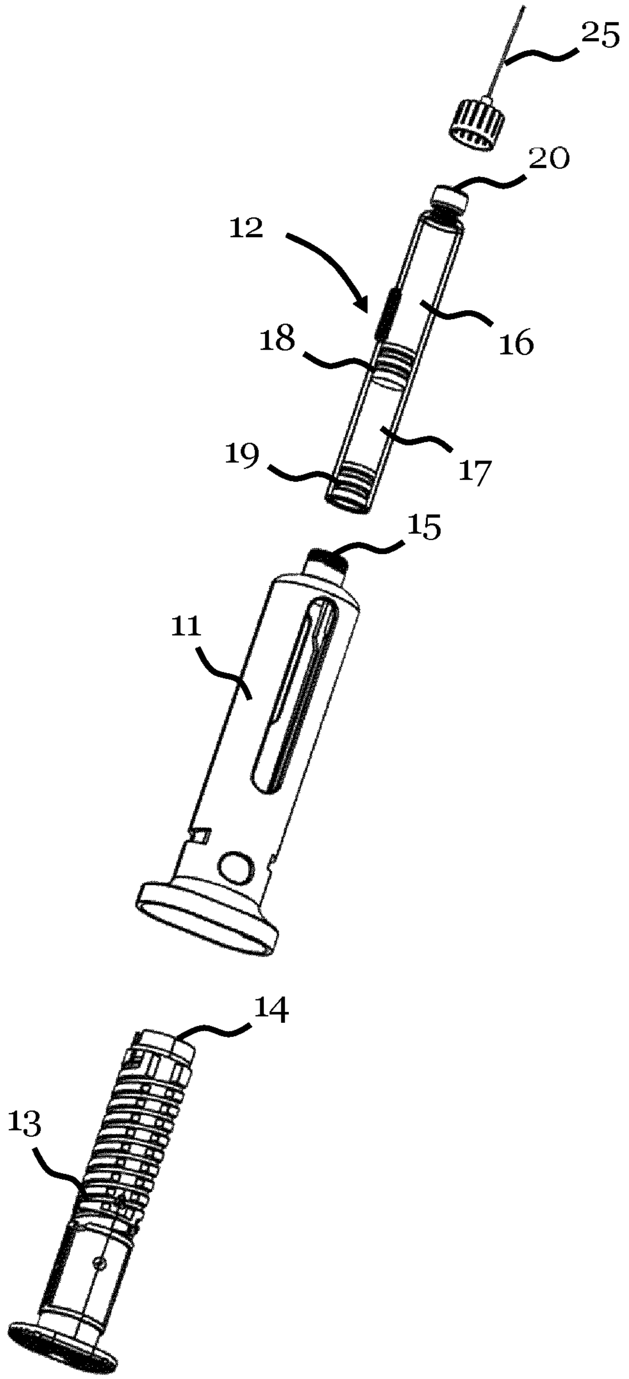
FIG. 1B illustrates the medicament delivery device of FIG. 1A in an exploded view.

FIG. 1A shows a perspective view illustrating a medicament or drug delivery device 10 in the form of an injector comprising a sub-assembly medicament delivery device according to an embodiment, while FIG. 1B illustrates the medicament delivery device 10 in an exploded view. Embodiments may be implemented in other types of medicament delivery devices, such as for instance inhalers and medical sprayers.

The device 10 comprises a main body 11 configured to accommodate a medicament, for instance contained in a container 12, e.g., a cartridge or a syringe, and a plunger rod 13 configured to move inside the main body 11 upon a user pushing a plunger rod. The main body 10 extends along a longitudinal axis between a proximal end where a medicament delivery member, e.g., a needle, is configured to be arranged at and a distal end where the plunger rod 13 is configured to pass through. The plunger rod 13 extends along the longitudinal axis between a proximal end and a distal end. The proximal end of the plunger rod is configured to act on the medicament container to expel the accommodated medicament. Moreover, the device 10 comprises an outlet to which a needle 25 is attached, via which needle 25 the medicament is delivered from the medicament container 12 upon the user pushing the plunger rod 13 to cause the plunger rod 13 to move into the main body 11 and push against the medicament container 12.

As shown in FIG. 1B, in this particular example the medicament container is a multi-chamber container. For example, the container 12 comprises two chambers where one chamber 16 comprises a first substance while the other chamber 17 comprises a second substance, which substances are mixed before administration as will be described. The container 12 further comprises a first stopper 18, a second stopper 19 and a container cap 20 being penetrated by the needle 25 upon the user attaching the needle 25 to the device output 15. The plunger rod 13 is configured to be pushed by the user against the second stopper 19, which in its turn will move inside the container 12 and a proximal end 14 of the plunger rod 13 will press against the second stopper 19, thereby causing the medicament to be pushed towards the device output 15 and through the needle 25.

Figure 2:
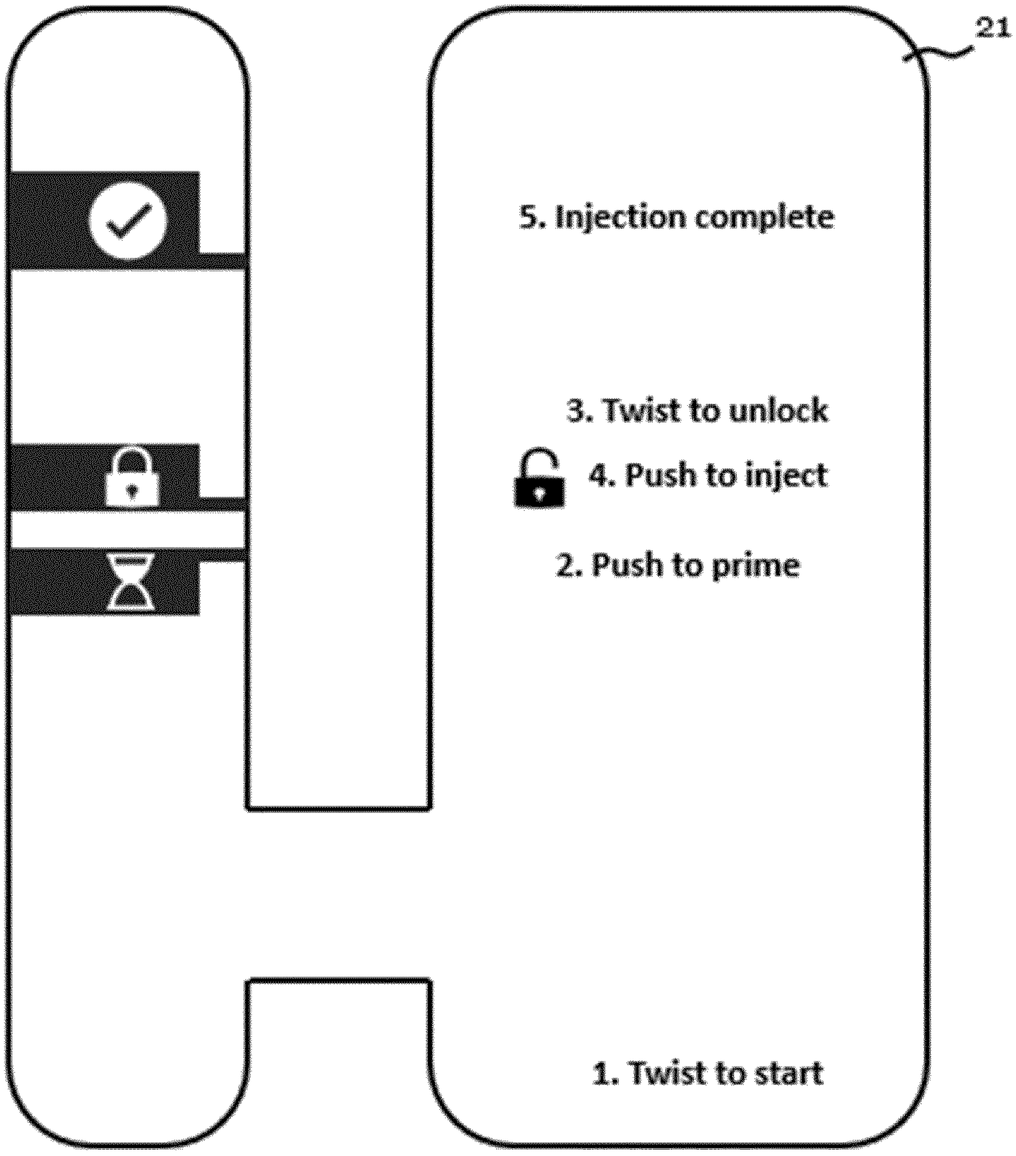
FIG. 2 illustrates a label comprising medicament delivery instructions required to be performed by the user for completing medicament delivery according to an embodiment, which label is to be attached to the injector of FIG. 1A.

With reference to FIG. 2, the sub-assembly of the medicament delivery device 10 according to embodiments is provided with a label 21 comprising multiple medicament delivery instructions required to be performed by the user for completing medicament delivery. It should be noted that this particular label 21 is exemplifying only and may take on many different appearances depending on the application.

In an embodiment, the label 21 is attached to an exterior of the main body 11 by means of adhesive. In another embodiment, without the label 21, the multiple instructions are attached directly to the exterior of the main body 11, for instance by means of printing. Alternatively, the multiple instructions can be multiple LED displays lined up to one another along a length of the exterior of the main body.

The label 21 of FIG. 2 comprises five different medicament delivery instructions arranged along a length of the exterior of the main body 11. The medicament delivery instructions are performed in a sequence one at a time, where each instruction is required to be performed by the user to complete the medicament delivery:

1. Twist to start (TTS),
2. Push to prime (PTP),
3. Twist to unlock (TTU),
4. Push to inject (PTI), and
5. Injection complete (IC).

Furthermore, the plunger rod comprises a first visual indication 24. In one example, the first visual indication 24 is arranged at the proximal end of the plunger rod 13. In one example, the first visual indication 24 is the proximal end of the plunger rod 13. In this example, the proximal end of the plunge rod 13 might be painted with a color that is different from a color of the other part of the plunger rod and the main body. Preferably, the color is bright, e.g., yellow or red. Alternatively, the first visual indication can be a component that is independent from the plunger rod and that has been attached to the proximal end of the plunger rod.

In a preferred example, at least one of the medicament delivery instructions can be provided on a certain portion of the main body, as most of the types of movement need to be continuously carried out in a period. For example, the 'Twist to start" movement might be designed such that the user needs to twist the plunger rod for 30 degrees around the longitudinal axis; in this example, the instruction can be one narrow line at least partially around the main body. Alternatively, the 'Twist to start" movement might be designed such that the user needs to twist the plunger rod three whole rounds relative to the longitudinal axis; in this example, the instruction can be a thick stripe occupying an indication length of the exterior of the main body. In a preferred example, the indication length is equal to a length that the plunger rod is configured to be moved forward after being twisted to rotate three rounds relative to the longitudinal axis.

Now, with reference to FIGS. 3A-E, a complete medication delivery process will be described in more detail where for dimensional reasons only the number and abbreviation of each instruction is illustrated throughout FIGS. 3A-E.

Figure 3A:
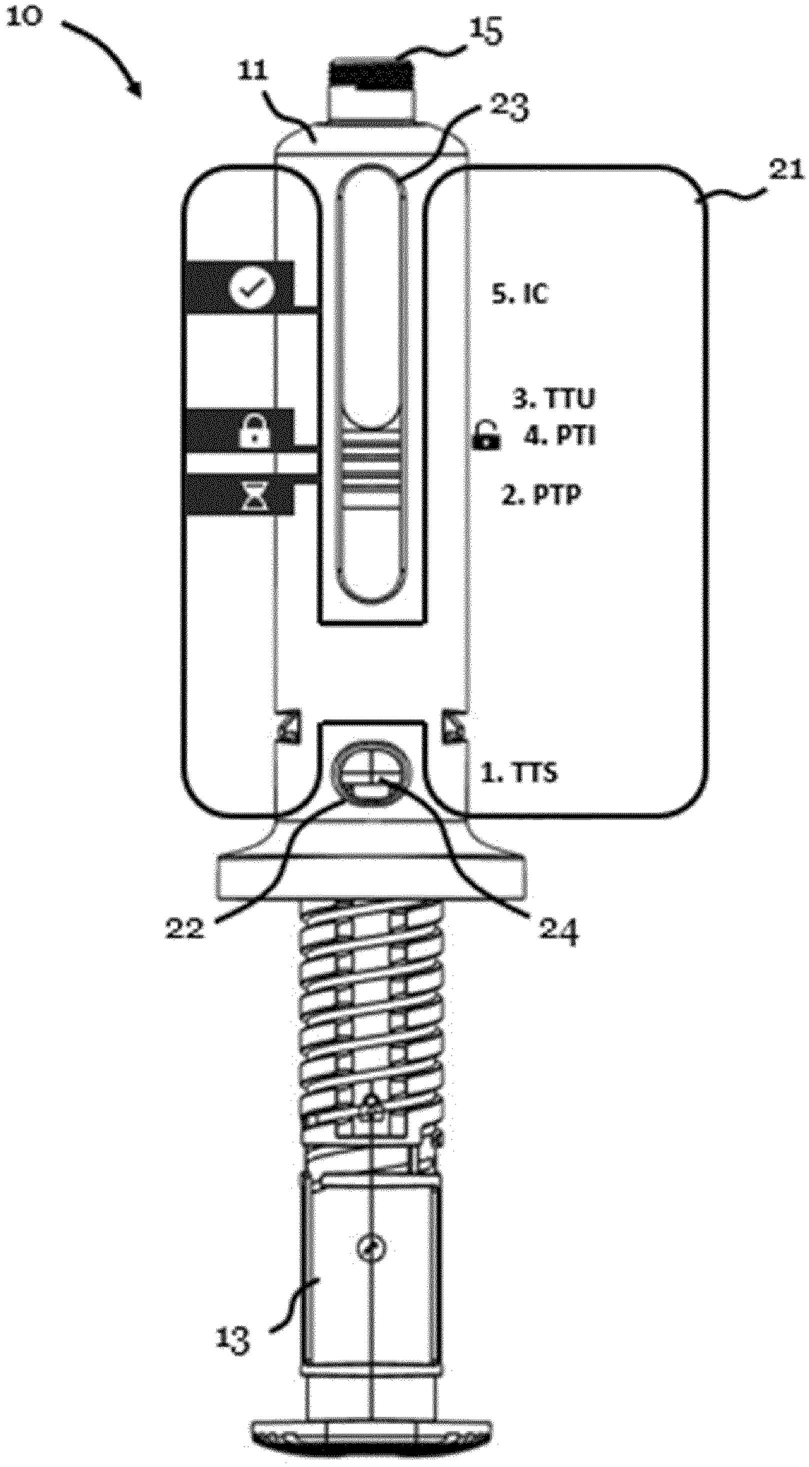
FIGS. 3A-E illustrate a process for delivering a medicament by performing the instructions on the label of FIG. 2 according to an embodiment.

Thus, in FIG. 3A, a device 10 is shown in the mode as initially delivered to the user and ready to be used. In this particular embodiment, the first instruction is "Twist to start" where the plunger rod 13 is in a locked state and cannot be pushed inside the main body 11, but must be twisted to be unlocked and further perform to mix the substances in the double chamber of the container 12 before administration. In this particular implementation, the plunger rod 13 must be rotated, i.e. twisted, relative to the main body 11 a number of rounds to enter an unlocked state. The locking mechanism will be described in more detail below. It may be envisaged that the user must insert the plunger rod 13 inside the main body 11 and push the plunger rod 13. It is noted that the user has yet not attached the needle to the device output 15.

In the embodiments illustrated, the main body 11 comprises a main window 23. The user can observe the accommodated medicament through the main window 23.

In the embodiments illustrated, the main body 11 comprises a second window 22 aligned with respect to the longitudinal axis of the main body 11 and arranged on a same side of the main body 11. The main window 23 and/or the second window 22 may be formed by one or two openings in a wall of the main body 11, or by one or two sections of the main body 11 that are formed by transparent material. However, it is envisaged that the main body 11 alternatively may comprise a single instruction window extending along its length. The main body 11 is arranged with the instruction window(s) to allow the user to observe the plunger rod 13 moving inside the main body 11. As the plunger rod 13 is configured to move into the main body, the first visual indication 24 of the plunger rod 13 is configured to be seen through the main window 23.

Figure 4:
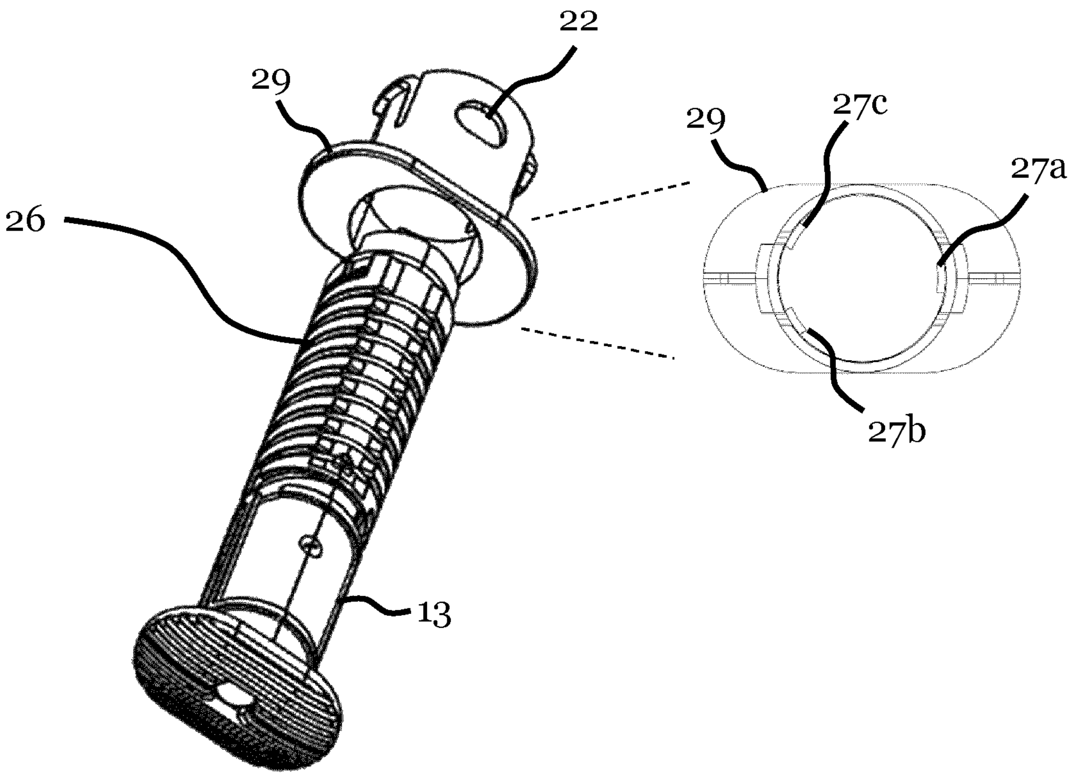
FIG. 4 illustrates a plunger rod according to an embodiment.

FIG. 4 illustrates the plunger rod 13 in an embodiment comprising an engagement member in the form of a track 26 being arranged to extend at least partly along a length of an exterior side of the plunger rod 13.

Accordingly, the main body 11 comprises at least one counter-engagement member in the form of a rib arranged on an interior side of the main body 11.

In this exemplifying embodiment, an insert 29 is arranged in the main body 11. Further as can be seen in the right-hand illustration showing the insert 29 from a perspective of an inlet side, the plunger rod 13 is inserted into the insert 29 and thus the main body 11. Further in this example, the insert 29 comprises three ribs 27*a-c* configured to engage with the thread 26 upon the user rotating the plunger rod 13 to cause the plunger rod 13 to move into the main body 11.

Thus, the plunger rod 13 is configured to move axially into the main body 11 with a rotation relative to the main body 11 via engagement between the track 26 and the ribs 27*a-c*.

As is understood, even though embodiments will be discussed in the following where the plunger rod 13 comprises the track 26 while the insert 29 comprises the ribs 27*a-c*, the opposite scenario is alternatively envisaged to attain the same functionality—i.e. the main body 11 (or the insert 29) would comprise the track 26, while the plunger rod 13 would comprise the ribs 27*a-c*.

As previously mentioned, tactile and/or audible feedback may be given to the user when the plunger rod 13 enters and/or exits the unlocked state and/or moves into or out of alignment with one or more instructions along the main body 11, which will be described in detail later.

Track 26 comprises multiple sections; wherein each of the multiple sections is shaped to guide the plunger rod 13 to be moved with a type of movement relative to the main body 11 such that the plunger rod 13 can only be moved in the proximal direction with the type of movement; and wherein each section of the track 26 is arranged at a location relative to a location of one of the medicament delivery instructions such that the user can only perform the type of movement instructed by the instruction aligned with the first visual indication 24 of the plunger rod 13 to move the plunger rod 13 in the proximal direction.

Figure 5:
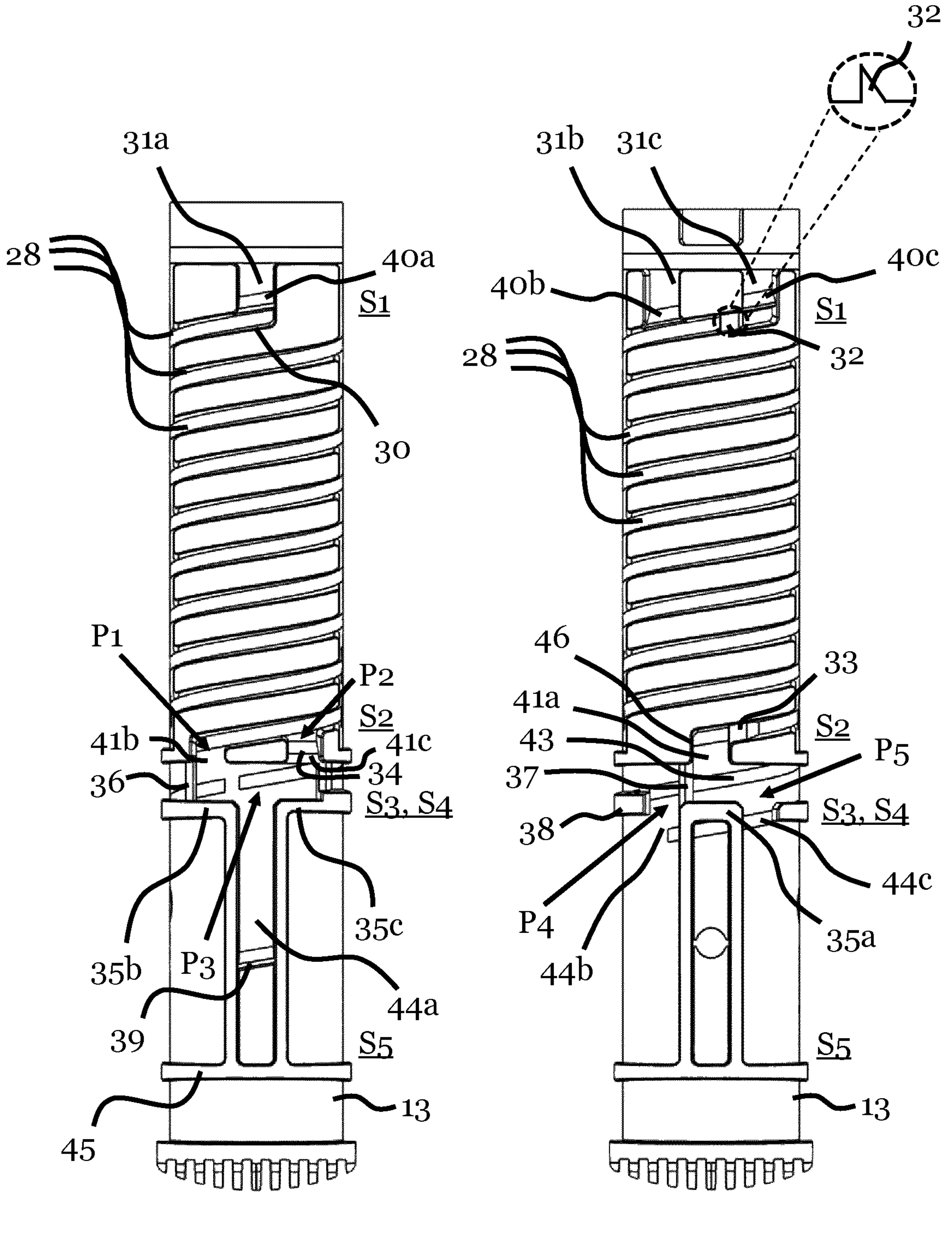
FIG. 5 illustrates the movement of the plunger rod of FIG. 4 according to an embodiment.

FIG. 5 illustrates two different opposing side views of the plunger rod 13. In the initial state previously described with reference to FIG. 3A, the track 26 comprises a first set of grooves 31*a-c* extending axially and connecting to a first end of a helical groove 28 to allow the first, second and third rib 27*a-c*, respectively, shown in FIG. 4 to slide into engagement with the helical groove 28 upon the user pushing the plunger rod 13 axially into the main body 11 as indicated at S1. Those grooves form the multiple sections of the track 26.

As understood, in one example where the multiple sections of the track comprise the number of first axial grooves 31*a-c*, the number of first axial grooves 31*a-c* will correspond to the number of ribs 27*a-c* being utilized. The first axial grooves 31*a-c* are configured to guide the plunger rod to be moved in the proximal direction only with a linear axial movement. For instance, if a single rib should be utilized, a single first groove will correspondingly be used, if two ribs should be utilized, a set of two first grooves will correspondingly be used, and so on.

Thus, in the initial state of FIG. 3A, the plunger rod 13 will be pushed into the main body 11 and the first rib 27*a* will slide into a first one 31*a* of the grooves comprised in the set of first axial grooves until the movement of the plunger rod 13 is stopped by the first rib 27*a* moving into contact with a first inner wall stop surface 30 of the helical groove 28. Simultaneously, the second rib 27*b* will slide into a second one 31*b* of the grooves in the first set of grooves while the third rib 27*c* slides into a third one 31*c* of the grooves and subsequently abut corresponding inner wall stop surfaces of the helical groove 28. In this position, the inner walls of the helical groove 26 will act as stop surfaces for the ribs 27*a-c* for further axial movement as a next movement.

At this stage, the user will have to rotate the plunger rod 13 in a counter-clockwise direction which has as an effect that the second rib 27*b* abutting the inner wall stop surfaces of the helical groove 28 will traverse a slightly protruding first bump 32, thereby providing a clicking tactile feedback as the second rib 27*b* traverses the first bump 32 upon engaging with the helical groove 28. Thus, both an audible and a tactile feedback may be provided. Further, as is understood, the audible and tactile feedback may be provided already when the first bump 32 and the second rib 27*b* move into contact with each other.

In an embodiment, the multiple sections of the track comprise the first bump 32 (and possibly also bumps to be described in the following) which is arranged with a first side having a surface with an increasing inclination in a direction via which the first rib 27*a* traverses the first bump 32, thereby allowing the traversal. However, once the first bump 32 is traversed, reverse movement of the plunger rod 13 is prevented since the first bump 32 is arranged with an opposite second side having a surface facing a direction of movement of the first rib 27*a*. Thus, the user cannot accidentally rotate the plunger rod 13 in the opposite direction since the surface of the second side of the first bump 32 forms an abutment with a counter surface of the first rib 27*a-c* upon reverse movement of the plunger rod 13.

In one example, the multiple sections of the track comprise helical grooves. The helical grooves are configured to guide the plunger rod to be moved in the proximal direction with rotation. As previously described with reference to FIG. 3B, after having rotated the plunger rod 13 a number of rounds, the plunger rod 13 has moved into the main body 11 by means of the helical groove 28 moving in engagement with the three ribs 27*a-c* thereby transporting the plunger rod 13 into the main body 11 in order to align the first visual indication 24 of the plunger rod 13 with the second medicament delivery instruction "Push to prime".

As indicated by S2, the first rib 27*a* will align just before the first visual indication 24 of the plunger rod 13 with the second medicament delivery instruction "Push to prime" and move into contact with a second bump 33, and as the user further rotates the plunger rod 13, a clicking tactile feedback is provided as the first rib 27*a* traverses the second bump 33 and the first visual indication 24 moves into alignment with the second medicament delivery instruction. This indicates that the priming operation—where contained air is expelled from the medicament container—is complete.

Furthermore, in one example where the multiple sections of the track comprise second axial grooves 41*a-c*, the multiple sections of the track can comprise a circumferential groove 43. Simultaneously, the second rib 27*b* is at position P1 while the third rib 27*c* is at position P2. As can be seen at S2, in this position the first rib 27*a* and the second rib 27*b* abut a corresponding inner wall of the helical groove 28 (the first rib being blocked by the second stop surface denoted 46), so no further rotation is possible. However, second axial grooves 41a-c connect to a second end of the helical groove 28 which allow the ribs 27a-c to axially move to the circumferential groove 43 connecting to the second axial grooves 41a-c, upon the user pushing the plunger rod 13 into the main body 11.

As previously described with reference to FIG. 3C, the user axially pushes the plunger rod 13, and the third rib 27c at P2 will traverse a third bump 34 when relocating from S2 to S3 relative to the moving plunger rod 13, thereby providing a further clicking tactile feedback to indicate the start of priming.

The plunger rod 13 thus moves into the main body 11 until the first visual indication 24 aligns with the third and fourth instructions thereby again moving the plunger rod 13 into the locked state as indicated at S3 where the first rib 27a is blocked by a first axially protruding stop surface 35a of the circumferential groove 43 while the second rib 27b and the third rib 27c abuts a second stop surface 35b and a third stop surface 35c, respectively, of the circumferential groove 43 to prevent the plunger rod 13 to move further axially into the main body 11.

Thus, as described with reference to FIG. 3D, the third instruction indicates "Twist to unlock" whereupon the user performs a 180°-rotation of the plunger rod 13.

Upon performing the 180°-twist at S3, the second rib 27b abutting the second stop 35b, will move in a left-hand direction along a circumferential axis of the circumferential groove 43, and traverse a fourth bump 36 to provide tactile feedback of the start of the "Twist to unlock"-movement.

After the 180°-rotation of the plunger rod 13, the first rib 27a has moved into position P3, while the second rib 27b and the third rib 27c have moved into positions P4 and P5, respectively, as indicated at S4. As can be seen, just before the second rib 27b relocates to position P4, it traverses a fifth bump 37 providing feedback to the user of the end of the "Twist to unlock"-movement before abutting a second radially protruding stop surface 38 located in the circumferential groove 43.

The final push can now be performed as previously described with reference to FIG. 3E in that the plunger rod 13 is pushed by the user into the main body 11 having the ribs 27a-27c engage with and move along third axial grooves 44a-c connecting to a second end of the circumferential groove 43 until the first visual indication 24 of the plunger rod 13 aligns with the final fifth instruction "Injection complete.

Hence, upon the plunger rod 13 being pushed, the first rib 27a traverses a sixth bump 39 providing a tactile indication of the end of medicament delivery before the plunger rod 13 has reached its final location as indicted at S5 and abuts at a radially protruding stop surface 45 located in the third axial grooves 44a-c.

Optionally, unless the medicament delivery device 10 is delivered to the user with the plunger rod 13 already mounted in the main body 11, three assembly retention bumps 40a-c may be arranged in the respective first grooves 31a-c to indicate to the user by means of tactile feedback that he/she correctly has inserted the plunger rod 13 into the main body 11.

As can be concluded, the bumps 32, 33, 34, 36, 37, 39, 40a-c are arranged along the track 26 at locations relative to locations of the medicament delivery instructions such that the bumps are traversed by the ribs 27a-c one after another before the first visual indication 24 aligns with a medicament delivery instruction along the main body 11 and after the first visual indication 24 moves out of alignment with a medicament delivery instruction. In a preferred example, each bump is arranged close to a location of the medicament delivery instruction that the first visual indication 24 is configured to align with. For example, each bump is arranged next to a location of a medicament delivery instruction, so that the user can get an audible/tactile indication right before and/or after aligning the first visual indication 24 with a medicament delivery instruction. For instance, the bumps may be arranged along the track such that the ribs traverse the bumps about 1-5 mm before the first visual indication aligns with a medicament delivery instruction and about 1-5 mm after the first visual indication moves out of alignment with a medicament delivery instruction. It should be noted that, the exact position of each bump is dependent on the design about when the audible/tactile indication should be provided.

Correspondingly, the stops 30, 35a-c, 38, 45, 46 are arranged along the track 26 such that if the plunger rod 13 has been axially pushed into the main body for the first visual indication 24 to move into alignment with a location of a medicament delivery instruction, a rotational movement of the plunger rod 13 must be performed as a next movement to have the rib(s) 27a-c move out of abutment with the stop surface and further along the track 26, while if the plunger rod 13 has been rotated relative to the main body 11 for the first visual indication 24 to move into alignment with a location of a medicament delivery instructions, an axial push of the plunger rod 13 must be performed as a next movement to have the rib(s) 27a-c move out of abutment with the stop surface and further along the track 26.

With the structural guide provided by the track 26 as mentioned above, the device with the sub-assembly of the invention can be operated as described below. As shown in FIG. 3A, the plunger rod 13 is arranged with the first visual indication 24 aligning with the current medicament delivery instruction ("TTS") in the first instruction window 22. The first visual indication 24 may be formed by a proximal end (denoted 14 in FIG. 1B) of the plunger rod 13 being pushed further into the main body 11. As discussed, in this example the first instruction is "Twist to start", whereupon the user rotates the plunger rod 13 a number of rounds-tactile feedback may be given to the user when the plunger rod enters the unlocked state as will be described subsequently—to unlock the device 10. As mentioned above, the track 26 provides the structural guide that if the user doesn't perform the correct instructed step, for example if the user doesn't twist the plunger rod with the instructed number of rounds, the movement of the next step cannot be carried out.

Figure 3B:
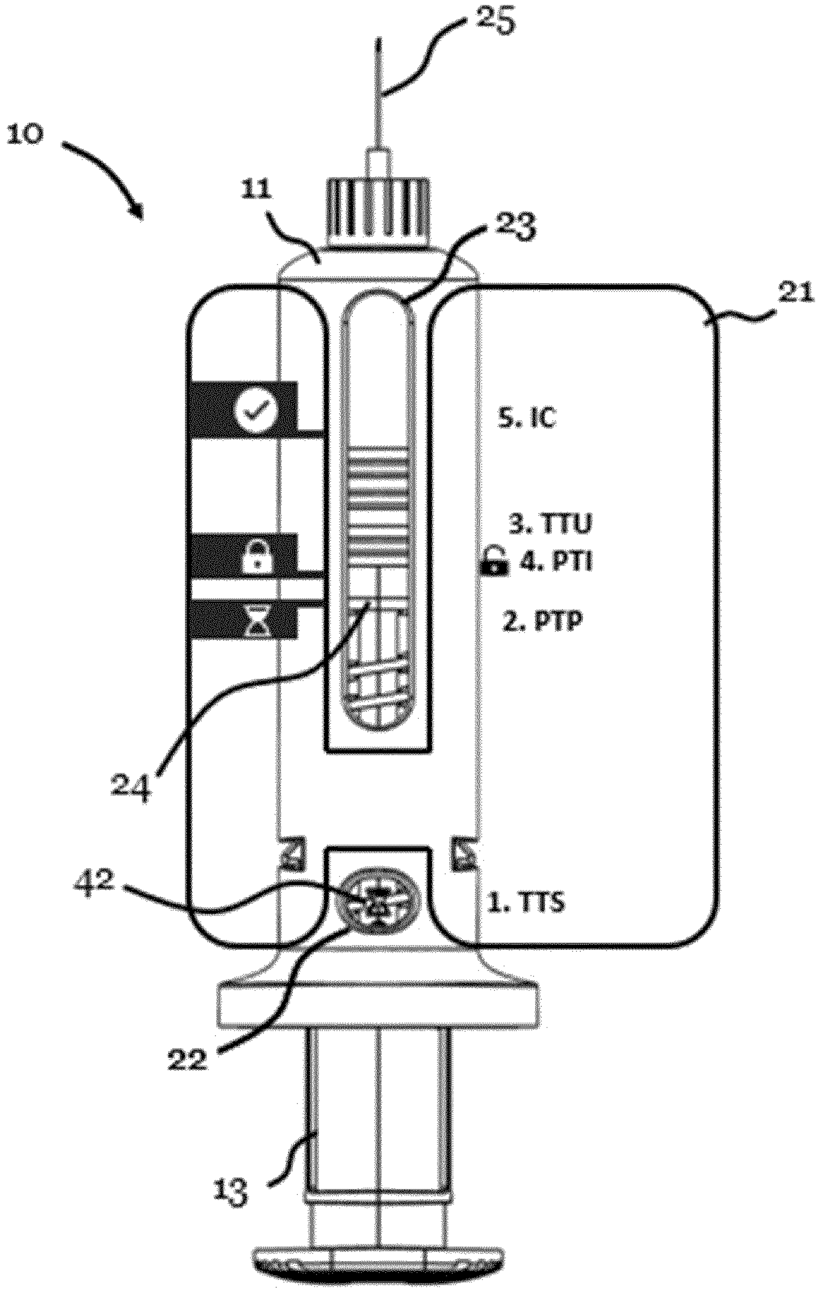

With reference to FIG. 3B, after the user having rotated the plunger rod 13 the required number of rounds, the first visual indication 24 of the plunger rod 13 has moved along the length of the main body 11 and aligns with a next location providing the second medicament delivery instruction "Push to prime." The user attaches the needle 25 to the device output before the priming.

In in alternative embodiment, the plunger rod 13 is not in the locked state initially in which case the first instruction located at the first instruction window 22 may be to push the plunger rod 13 until the first visual indication 24 of the plunger rod 13 aligns with the second medicament delivery instruction "Push to prime", or the plunger rod 13 may initially be located further inside the main body 11 and aligns with "Push to prime" being the first instruction.

As understood, an advantage of providing the locked plunger rod state as initial device mode is that an unintentional movement of the plunger rod can be prevented.

On the other hand, an advantage of not providing the locked plunger rod state as initial device mode is that the device is easy to use. This may advantageously allow the user the perform the medicament delivery using only one hand.

Optionally, as illustrated on a left-hand side of the second instruction window 23, e.g. a symbol, (in the form of an hourglass in the example as shown in FIG. 3B) is provided on the label 21 to indicate to the user that he/she should wait before proceeding to the next instruction.

Further optionally, it may be envisaged that a specific time period is provided in connection to the symbol, such as e.g. 30 seconds.

Yet further optionally, as shown in FIG. 3*b*, the plunger rod 13 is provided with a second visual indication 42, in this example an hourglass symbol, appearing in the first instruction window 22 upon the plunger rod 13 being moved to the location along the main body 11 where the first visual indication 24 aligns with the second instruction.

Figure 3C:
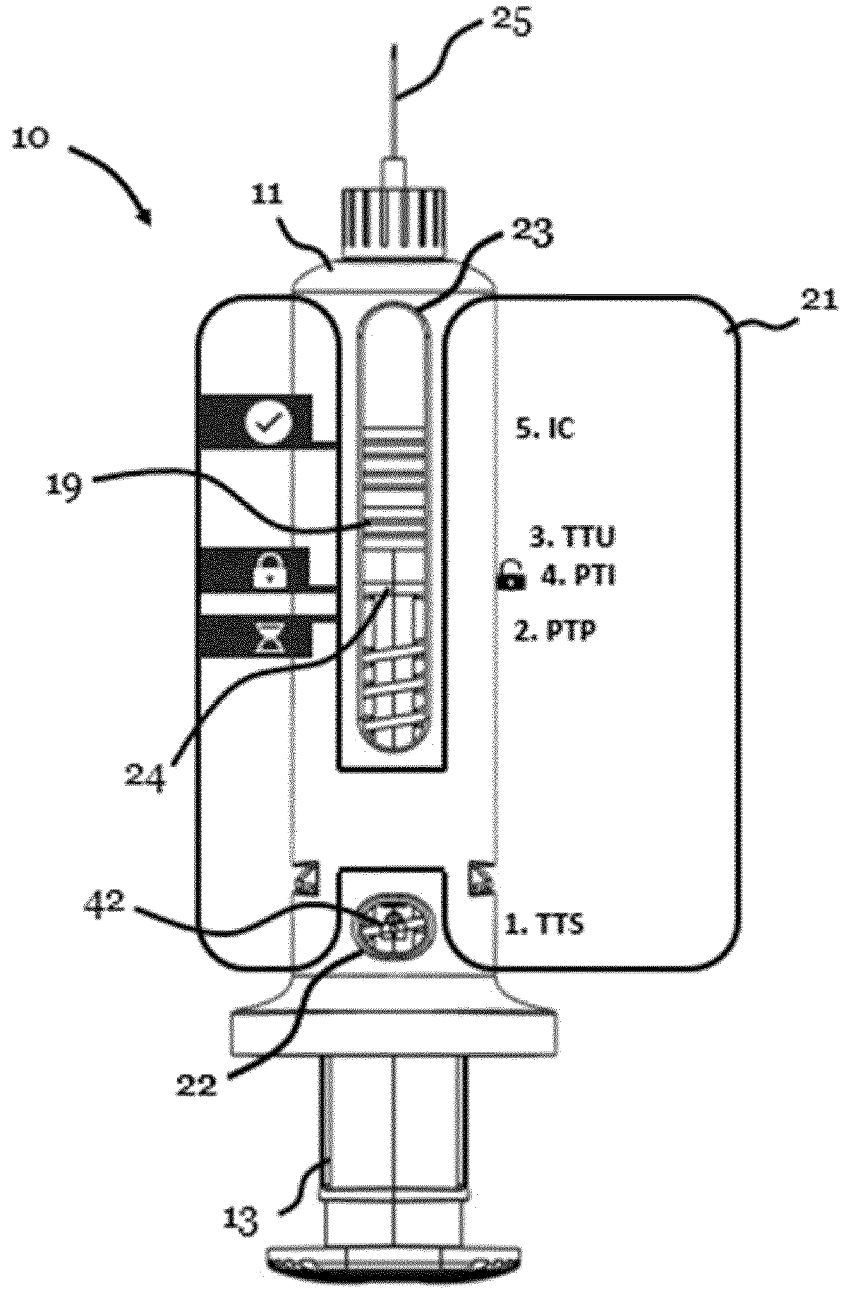

As shown in FIG. 3C the user pushes the plunger rod 13 to a next location along the main body 11 to align the first visual indication 24 with the associated next set of instructions; third instruction "Twist to unlock" and fourth instruction "Push to inject".

With the priming movement, the user pushes the plunger rod 13 against the first stopper 19 to transport the medicament towards the outlet and the needle 25 thereby removing any undesired air pockets occurring at the device outlet. After the priming, the device 10 is setup for delivering medicament to the user.

Optionally, the plunger rod 13 is provided with a lock symbol as the second visual indication 42, which appears in the first instruction window 22 upon the plunger rod 13 being moved to the location along the main body 11 where the first visual indication 24 aligns with the third and fourth instructions.

Further optionally, as illustrated on a left-hand side of the second instruction window 23, a symbol in the form of a lock is provided on the label 21 to indicate to the user that he/she will need to unlock the plunger rod 13 before proceeding to the next instruction, i.e. to perform the third instruction "Twist to unlock".

Figure 3D:
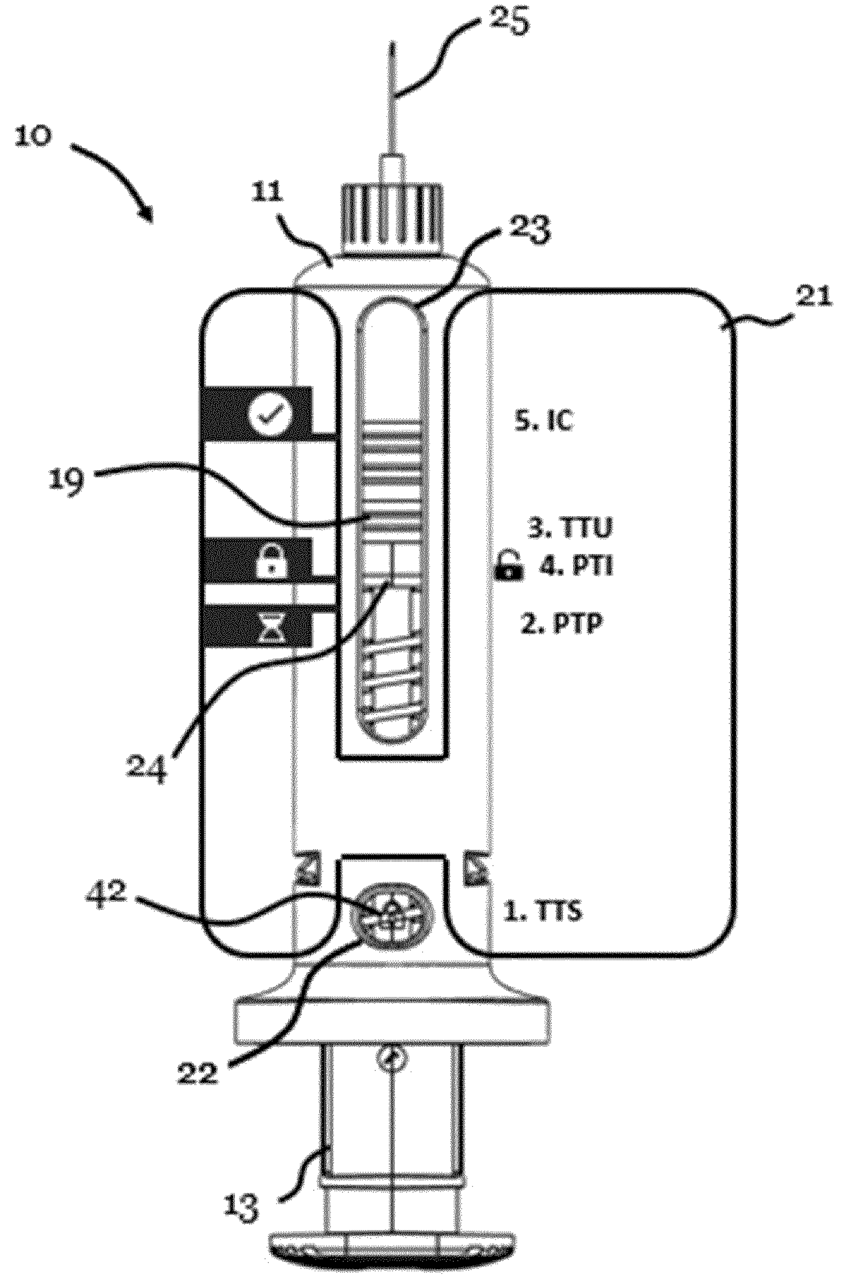

FIG. 3D shows the device after the fourth instruction "Twist to unlock" has been performed by the user performing a 180°-rotation of the plunger rod 13. The plunger rod 13 is provided with an unlock symbol as the second visual indication 42, which appears in the first instruction window 22. The label 21 is correspondingly provided with an unlock symbol on a right-hand side of the first visual indication 24.

Figure 3E:
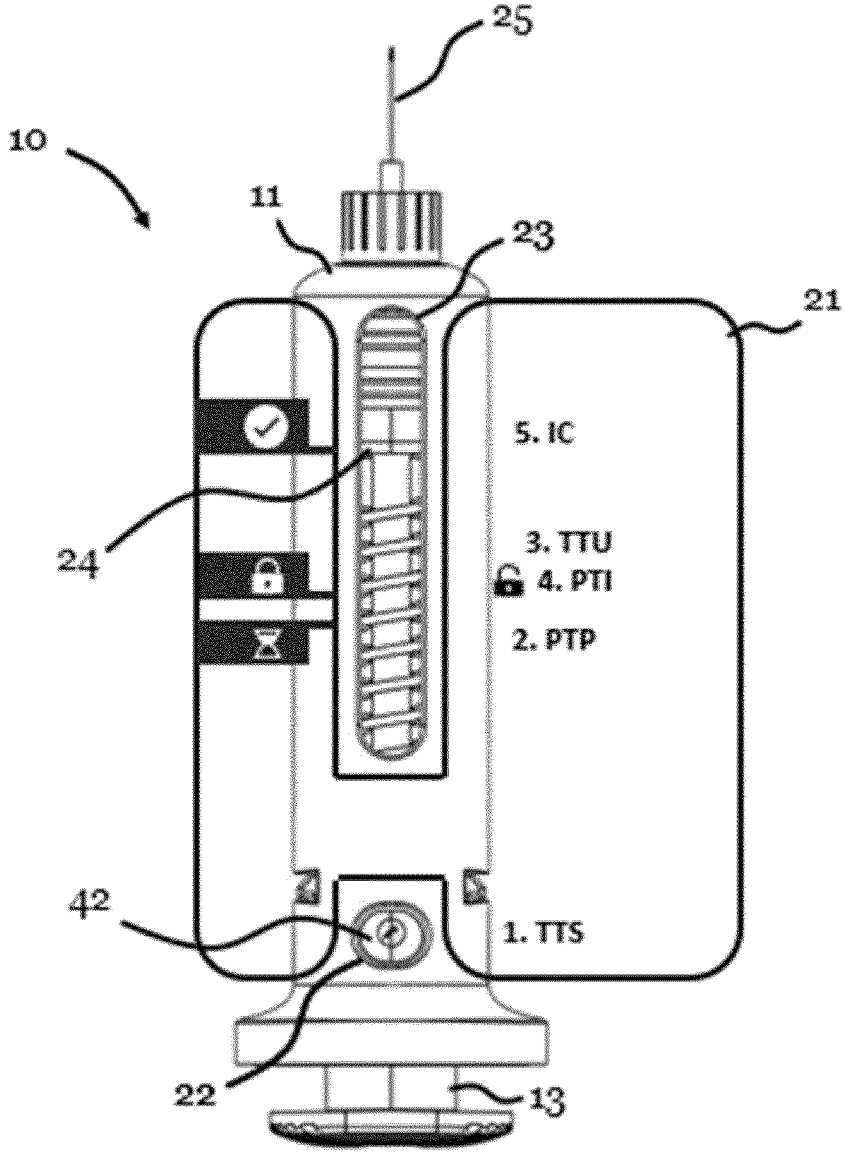

The user proceeds with fourth instruction "Push to inject" and pushes the plunger rod 13 into the main body until the first visual indication 24 aligns with the final instruction as shown in FIG. 3E; "Injection complete". The label 21 displays a checkbox on a left-hand side of the first visual indication 24 while a confirmation symbol appears in the first instruction window 22 as the second visual indication 42.

Thus, the medicament delivery is completed and the device 10 may be appropriately disposed.

As can be concluded, at each location with which the first visual indication 24 of the plunger rod 13 aligns by gradual user movement of the plunger rod 13 into the main body 11, either a single medicament delivery instruction is provided-such as instruction no. 1 in the initial position- or a group of medicament delivery instructions to be performed in an indicated sequence is provided—such as instructions no. 3 and 4 in the third position. The user proceeds with gradually moving the plunger rod 13 into the main body 11 until the final location and corresponding instruction no. 5 has been reached and the medicament delivery process is complete.

As shown throughout FIGS. 3A-E, the label 21 comprises four zones on a right-hand side in this exemplifying embodiment, each comprising one or more medicament delivery instructions. For instance, while a first zone comprises a single instruction ("TTS"), a third zone comprises two instructions ("TTU" and "PTI") further comprising an indication in which order the instructions should be performed upon the first visual indication 24 of the plunger rod 13 aligning with the third zone.

The medicament delivery device 10 is illustrated herein to deliver a single fixed dose, but the device could be adapted for variable fixed dose delivery. For instance, instead of performing "Twist to unlock" as the third instruction, the user could be allowed to set the dose by a fourth step presenting a number of fixed dose options as defined by the drug treatment, which dose options may be presented as graphics in the instruction windows.

The medicament delivery devices described herein can be used for the treatment and/or prophylaxis of one or more of many different types of disorders. Exemplary disorders include, but are not limited to: rheumatoid arthritis, inflammatory bowel diseases (e.g. Crohn's disease and ulcerative colitis), hypercholesterolaemia, diabetes (e.g. type 2 diabetes), psoriasis, migraines, multiple sclerosis, anaemia, lupus, atopic dermatitis, asthma, nasal polyps, acute hypoglycaemia, obesity, anaphylaxis and allergies. Exemplary drugs that could be included in the medicament delivery devices described herein include, but are not limited to (with non-limiting examples of relevant disorders in brackets): etanercept (rheumatoid arthritis, inflammatory bowel diseases (e.g. Crohn's disease and ulcerative colitis)), evolocumab (hypercholesterolaemia), exenatide (type 2 diabetes), secukinumab (psoriasis), erenumab (migraines), alirocumab (rheumatoid arthritis), methotrexate (amethopterin) (rheumatoid arthritis), tocilizumab (rheumatoid arthritis), interferon beta-1a (multiple sclerosis), sumatriptan (migraines), adalimumab (rheumatoid arthritis), darbepoetin alfa (anaemia), belimumab (lupus), peginterferon beta-1a' (multiple sclerosis), sarilumab (rheumatoid arthritis), semaglutide (type 2 diabetes, obesity), dupilumab (atopic dermatitis, asthma, nasal polyps, allergies), glucagon (acute hypoglycaemia), epinephrine (anaphylaxis), insulin (diabetes), atropine and vedolizumab (inflammatory bowel diseases (e.g. Crohn's disease and ulcerative colitis)). Pharmaceutical formulations including, but not limited to, any drug described herein are also contemplated for use in the medicament delivery devices described herein, for example pharmaceutical formulations comprising a drug as listed herein (or a pharmaceutically acceptable salt of the drug) and a pharmaceutically acceptable carrier. Pharmaceutical formulations comprising a drug as listed herein (or a pharmaceutically acceptable salt of the drug) may include one or more other active ingredients, or may be the only active ingredient present.

The aspects of the present disclosure have mainly been described above with reference to a few embodiments and examples thereof. However, as is readily appreciated by a person skilled in the art, embodiments other than the ones disclosed above are equally possible within the scope of the invention, as defined by the appended patent claims.

Thus, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A sub-assembly of a medicament delivery device comprising:

a main body configured to accommodate a medicament; and a plunger rod being moveable inside the main body along a length of the main body upon a user applying force to the plunger rod, wherein the main body comprises a main window through which the accommodated medicament is observable, wherein the main body is provided with multiple medicament delivery instructions along the length of an exterior of the main body, wherein each of the medicament delivery instructions is configured to instruct the user to move the plunger rod further into the main body with a type of movement to align a first visual indication of the plunger rod observable through said main window with a next medicament delivery instruction to be performed along the length of the main body, wherein the plunger rod comprises an engagement member at an exterior the plunger rod and the main body is operably arranged with a counter-engagement member at an interior the main body, wherein the plunger rod is configured to move into the main body via engagement between the engagement member and the counter-engagement member, wherein the engagement member is one of a track and at least one rib and the counter-engagement member is the other one of the track and the at least one rib, wherein the track comprises multiple sections, wherein each of the multiple sections is shaped to guide the plunger rod to be moved with a type of movement relative to the main body such that the plunger rod can only be moved in the proximal direction with the type of movement, and wherein each section of the track is arranged at a location relative to a location of one of the medicament delivery instructions such that the user can only perform the type of movement instructed by the instruction aligned with the first visual indication of the plunger rod to move the plunger rod in the proximal direction.

2. The sub-assembly of claim 1, wherein the main body comprises a second windows through which the plunger rod is observable upon moving along the length of the main body, the main window and the second window being arranged on a same side of the main body and aligned with respect to a longitudinal axis of the main body.

3. The sub-assembly of claim 2, wherein the plunger rod is arranged with at least one second visual indication on an exterior of the plunger rod, and the second window of the at least two windows is configured to display the at least one second visual indication while the main window of the at least two windows is configured to display the first visual indication of the plunger rod, said at least one second visual indication being related to the medicament delivery instruction with which the first visual indication of the plunger rod currently is aligned.

4. The sub-assembly of claim 1, wherein the main body comprises a counter-engagement member at an interior of the main body, wherein the plunger rod is configured to move into the main body via engagement between the engagement member and the counter-engagement member.

5. The sub-assembly of claim 1, the device comprising:

an insert attached to the main body, wherein the insert comprises the counter-engagement member to engage with said engagement member.

6. The sub-assembly of claim 1, wherein each of the multiple sections are shaped to guide the plunger rod to be moved with a linear movement or a helical movement relative to the main body such that the plunger rod is moved in the proximal direction with the linear movement or the helical movement.

7. The sub-assembly of claim 1, wherein:

the multiple sections of the track are at least one first axial groove connecting to one end of a helical groove and at least one second axial groove connecting to another end the helical groove.

8. The sub-assembly of claim 7, the track further comprising a circumferential groove connecting to the at least one second axial groove at one end of the circumferential groove, and at least one third axial groove connecting to the circumferential groove at another end of the circumferential groove, the circumferential groove further extending in an axial direction.

9. The sub-assembly of claim 8, wherein the plunger rod is configured to move further into the main body with a rotation relative to the main body via engagement between the at least one rib and the helical groove, and with an axial push into the main body via engagement between the at least one rib and either one of the at least one first axial groove, the at least one second axial groove, the circumferential groove and the at least one third axial groove.

10. The sub-assembly of claim 8, wherein an inner wall of the helical groove comprises at least one first stop surface at the end connecting to said at least one first axial groove for blocking the at least one rib from further axial movement as a next movement, and a second stop surface at the end connecting to said at least one second axial groove for blocking the at least one rib from further rotational movement as a next movement, the circumferential groove comprises at least one first radially protruding stop surface at the end connecting to said at least one third axial groove for blocking the at least one rib from further axial movement as a next movement, and at least one second radially protruding stop surface along a circumferential axis for blocking the at least one rib from further rotational axial movement as a next movement after a 180° rotational movement have been performed upon said at least one rib member being blocked by the at least one first radially protruding stop surface of the circumferential groove, and the at least one third axial groove comprises at least one first radially protruding stop surface for blocking the at least one rib from any further movement into the main body.

11. The sub-assembly of claim 8, wherein said at least one first axial groove, said helical groove, said at least one second axial groove, said circumferential groove and said at least one third axial groove comprises at least one bump over which the at least one rib traverses upon the user moving the plunger rod into the main body.

12. The sub-assembly of claim 6, wherein the track comprises at least one bump over which the at least one rib traverses upon the user moving the plunger rod into the main bod.

13. The sub-assembly of claim 11, wherein the track comprises multiple bumps, the bumps are arranged along the track at locations relative to locations of the medicament delivery instructions such that the bumps are traversed by the at least one rib one after another before the first visual indication aligns with a medicament delivery instruction along the main body and after the first visual indication moves out of alignment with the medicament delivery instruction along the main body.

14. The sub-assembly of claim 1, wherein the multiple medicament delivery instructions are one of printed instructions on the main body, printed instructions attached to the main body, instructions formed by multiple protrusions extending from the main body, instructions formed by multiple recesses in a wall of the main body, and instructions formed by multiple protrusions attached to the main body.

15. The sub-assembly of claim 1, wherein the first visual indication is arranged at the proximal end of the plunger rod.

* * * * *